(12) United States Patent
Spasovski

(10) Patent No.: US 11,717,354 B1
(45) Date of Patent: Aug. 8, 2023

(54) DEVICE AND METHOD FOR DISPLAYING THE AXIS OF ASTIGMATISM OF AN EYE

(71) Applicant: CHRONOS VISION GMBH, Berlin (DE)

(72) Inventor: Saso Spasovski, Berlin (DE)

(73) Assignee: CHRONOS VISION GMBH, Berlin (DE)

( * ) Notice: Subject to any disclaimer, the term of this patent is extended or adjusted under 35 U.S.C. 154(b) by 1168 days.

(21) Appl. No.: 16/368,081

(22) Filed: Mar. 28, 2019

Related U.S. Application Data

(63) Continuation of application No. PCT/DE2017/000320, filed on Sep. 24, 2017.

(30) Foreign Application Priority Data

Sep. 30, 2016 (DE) ............... 10 2016 011 759.1

(51) Int. Cl.
| | |
|---|---|
| *A61B 90/20* | (2016.01) |
| *A61B 34/00* | (2016.01) |
| *A61B 3/103* | (2006.01) |
| *A61F 2/16* | (2006.01) |
| *A61F 9/008* | (2006.01) |

(Continued)

(52) U.S. Cl.
CPC ............ *A61B 34/25* (2016.02); *A61B 3/1035* (2013.01); *A61B 90/20* (2016.02); *A61F 2/1645* (2015.04); *A61F 2/1662* (2013.01); *A61F 9/008* (2013.01); *A61B 2034/2048* (2016.02); *A61B 2034/252* (2016.02); *A61B 2090/373* (2016.02); *A61B 2505/05* (2013.01); *A61B 2560/0475* (2013.01); *A61F 2009/00844* (2013.01)

(58) Field of Classification Search
None
See application file for complete search history.

(56) References Cited

U.S. PATENT DOCUMENTS

| | | | |
|---|---|---|---|
| 2008/0204864 A1 | 8/2008 | Sander | |
| 2011/0019151 A1* | 1/2011 | Schuhrke | ............... A61B 3/111 |
| | | | 351/246 |

(Continued)

FOREIGN PATENT DOCUMENTS

| | | |
|---|---|---|
| DE | 10 2007 009 543 A1 | 8/2008 |
| WO | WO 2012/041349 A1 | 4/2012 |
| WO | WO 2015/176699 A2 | 11/2015 |

OTHER PUBLICATIONS

Ventura et al., "Surgical management of astigmatism with toric intraocular lenses," Arquivos Brasileiros de Oftalmologia, vol. 77, No. 2, pp. 125-131, Apr. 2014.

(Continued)

*Primary Examiner* — Eileen M Adams
(74) *Attorney, Agent, or Firm* — KDW Firm PLLC

(57) ABSTRACT

The invention relates to a device and a method for displaying the axis of astigmatism of an eye, in which an observation unit is used to observe the eye and, using a display unit, the orientation of the axis of astigmatism of the eye is displayed. A sensor unit generates sensor data which indicate a modification to the alignment of the observation unit relative to the eye. A calculation unit updates the displayed orientation of the axis of astigmatism with the aid of the sensor data, and issues it as the current orientation of the display unit.

20 Claims, 3 Drawing Sheets

(51) Int. Cl.
*A61B 90/00* (2016.01)
*A61B 34/20* (2016.01)

(56) References Cited

U.S. PATENT DOCUMENTS

| | | | |
|---|---|---|---|
| 2011/0157553 A1* | 6/2011 | Moeller | A61B 3/113 |
| | | | 351/209 |
| 2011/0230751 A1 | 9/2011 | Kersting | |
| 2012/0022408 A1 | 1/2012 | Hubschman et al. | |
| 2014/0003661 A1* | 1/2014 | Kwon | H04N 23/61 |
| | | | 382/103 |
| 2015/0077528 A1 | 3/2015 | Awdeh | |
| 2015/0305786 A1* | 10/2015 | Wehrle | A61B 17/7083 |
| | | | 606/86 A |
| 2017/0215726 A1 | 8/2017 | Spasovski et al. | |
| 2017/0333141 A1* | 11/2017 | Itkowitz | A61B 34/25 |

OTHER PUBLICATIONS

International Search Report and Written Opinion for Application No. PCT/DE2017/000320 dated Apr. 5, 2018.

\* cited by examiner

DEVICE AND METHOD FOR DISPLAYING THE AXIS OF ASTIGMATISM OF AN EYE

CROSS-REFERENCE TO RELATED APPLICATIONS

This application is a continuation of PCT/DE2017/000320 filed Sep. 24, 2017, which claims the benefit of and priority to German Patent Application No. 10 2016 011 759.1 filed Sep. 30, 2016, the entire disclosures of which are herein incorporated by reference.

TECHNICAL FIELD

Knowledge of the accurate orientation and position of the eye is important in eye surgery, with accurate knowledge of the torsion of the eye, in particular, being of decisive importance. Said eye surgery includes, for example, laser in situ keratomileusis (LASIK) or the use of toric intraocular lenses in cataract operations, which correct an astigmatism of the eye.

BACKGROUND

Toric intraocular lenses, abbreviated TIOL, have no spherical geometry. They are characterized by a maximum and a minimum curvature (principal curvatures) along two meridians through the apex that extend perpendicular to one another. The direction with the greatest curvature is denoted by markings, which are situated on the TIOL surface and the nature of which varies between producers.

The optimal torsional orientation of the two directions of principal curvature of the TIOL is patient-specific and depends on the orientation or direction of the corneal axis of astigmatism of the eye. A complete compensation of the astigmatism is achieved if the physician aligns the direction denoted by markings or surface markings on the TIOL with the axis of astigmatism of the eye.

Consequently, the success of an operation depends decisively on exact knowledge of the situation of the axis of astigmatism of the patient during the implantation of the TIOL and on presentation of the latter to the physician.

A guidance system is attached to the surgical microscope for the purposes of carrying out eye surgery, said guidance system providing the physician with detail data in respect of the eye, such as, e.g., the orientation and position thereof in relation to the microscope or surgical microscope.

The intraoperative indication of the axis of astigmatism of the eye during the operation assists the physician with the insertion of the toric intraocular lenses or TIOLs, which compensate the astigmatism or astigmatic refractive error of the cornea of the eye.

A number of methods that are used for this purpose are known. These methods can be subdivided into manual methods, image processing methods and measurement methods.

In the manual methods, which are most frequently used by far, the axis of astigmatism of the patient is determined preoperatively during a diagnosis with a keratograph, for example, and stored as an angle from the horizontal as a measurement value. On the day of the operation, the orientation of the axis of astigmatism or the axis orientation is applied to the eye surface of the seated patient manually by means of a stamp. During the operation, this marking is visible through the eyepiece of the surgical microscope and can be used by the physician as an orientation aid during the lens implantation.

However, these methods are disadvantageous in that the visibility of the marking may reduce over time, which may be caused by rinsing processes during the operation, for example. Furthermore, the accuracy of the angular orientation of the markings may suffer as a result of the manual nature of the application, often leading to inaccuracies. Moreover, the head alignment during the application of the marking may differ from the head alignment during the diagnosis, and so an offset error may arise as a result thereof.

In the methods based on image processing, a reference recording of the eye is made with the aid of a camera and stored at the same time as the diagnostic determination of the axis of astigmatism. The scleral blood vessels visible in the image, or else the iris pattern, are automatically searched for in current intraoperative images of the camera of the surgical microscope with the aid of a computer unit in order to determine the relative torsion of the eye through the viewing direction between the time of diagnosis and the time of surgery using matching and registration algorithms. Once this torsion has been ascertained, the current intraoperative orientation of the axis of astigmatism can be mirrored into the beam path of the microscope as an angular sum of the alignment during the diagnosis and the torsion and can thus serve the physician as an orientation aid.

However, a number of disadvantages arise in the process. Firstly, the lack of prominent blood vessels and iris structures may lead to the image processing algorithms only being able to determine the torsion to an insufficient extent, or even not at all. In this case, it is not possible to determine the current axis of astigmatism. Furthermore, bleeding during the operation may lead to the scleral blood vessels, which are clearly visible during the diagnosis, not being found in the current operation image. This renders a registration between diagnostic image and current operation image by way of prominent vessel structures impossible and the current axis of astigmatism cannot be ascertained. If there is an intraoperative change in the alignment of the microscope and the microscope camera connected therewith, for example if there is a rotation about the direction of observation, then a new calculation of the torsion is required so that the correct intended orientation of the TIOL to be implanted can be indicated. This method necessarily requires a reference image of the diagnostic time, which is not provided by all diagnostic appliances.

The third group, the measurement methods, includes more recent methods that require no reference images from the diagnosis since the situation or orientation of the axis of astigmatism is directly measured anew during the operation, when the patient already is in a lying position. Such a method is disclosed in the document WO2015176699A2, in which the astigmatism of the corneal surface is measured with the aid of a camera and an illumination unit. As a result, a registration by image processing between an image from the diagnosis and a current intraoperative image of the camera of the surgical microscope is dispensed with. The disadvantages of the above-described methods do not apply since the result does not depend on the accuracy of manually applied markings or on the simultaneous presence and quality of prominent structures in diagnostic image and operation image.

Other known measurement methods use wavefront aberrometry in order to determine the astigmatism of the eye.

However, the physician may change the orientation of the microscope or the microscope camera. After such a change, the operation can no longer be continued with the same coordinates with respect to the axis position of the astigmatism or errors arise with respect to the orientation of the TIOL. In this case, a renewed measurement of the axis of astigmatism is necessary so that the intended orientation of the TIOL to be implanted can be correctly indicated.

In practice, changes in the orientation of the microscope cannot be precluded during the operation, and so continuous computation is necessary during the image processing methods and a continuous measurement of the axis of astigmatism is necessary during the measurement methods. In the process, various factors, such as, e.g., occlusions, corneal reflections, foreign objects, bleeding, etc., may lead to a falsification of the calculated or measured results with respect to the axis position of the astigmatism.

If the axis of astigmatism is measured intraoperatively and before any intervention, with the patient situated in a lying position, the assumption can be made that the measured axis of astigmatism physically corresponds to the axis ascertained during the diagnosis. Now, a further difficulty lies in the fact that some steps in the operation may temporarily, or else permanently, change the orientation of the axis of astigmatism, for example if mechanical pressure is exerted on the eye or if incisions are made in the limbus for the purposes of opening the eye chamber. What results therefrom is that subsequent measurements of the axis of astigmatism no longer reproduce the original, i.e., preoperative, axis. As a consequence, the intended alignment of the TIOL to be inserted is no longer correctly indicated.

SUMMARY

It is an object of the invention to overcome the above-described disadvantages and provide the physician with correct information about the situation or alignment of the axis of the astigmatism to be corrected at all times during the operation. In particular, errors that arise on account of the orientation of the surgical microscope being able to change during the operation and on account of certain steps in the operation possibly causing a change in the axis of astigmatism should be avoided. Both of the aforementioned problems have previously yielded incorrect information about the orientation of the axis of the astigmatism to be corrected during the further course of the operation. Furthermore, the robustness when ascertaining the current axis position should be increased.

This object is achieved by the apparatus and method as disclosed herein.

The apparatus according to the invention for indicating the axis of astigmatism of the eye comprises an observation unit for observing the eye, an indication unit for indicating the orientation of the axis of astigmatism of the eye, a sensor device for producing sensor data that characterize a change in the alignment of the observation unit relative to the eye and a computing unit, which, with the aid of the sensor data, updates the orientation of the axis of astigmatism to be indicated and provides this as current orientation R' of the indication unit.

What this achieves is that the operation can be continued with correct data in the case of a change in the orientation of the observation unit in relation to the eye, in particular in the case of a torsion about the observation direction. In particular, the orientation of the actual axis of astigmatism of the eye continues to be indicated correctly after a change in the orientation of the observation unit.

A further advantage that arises is that there is no need for a diagnostic image. Even in the case of a change in the orientation of the axis of astigmatism as a result of steps in the operation, the orientation of the preoperative axis of astigmatism or the intended orientation of the TIOL to be implanted can be correctly specified at all times.

Moreover, the robustness when ascertaining the current axis position is increased. While errors and inaccuracies may occur as a result of occlusions, foreign objects, rinsing processes, etc., in the case of direct measurements and in the case of image processing, the solution according to the invention offers the advantage that it is completely insensitive to such influences since, for example, only the movement of the microscope is measured.

Advantageously, the observation unit comprises a surgical microscope or is configured as a surgical microscope.

In particular, the observation unit can comprise a camera for recording images of the eye or can be configured as a camera.

Advantageously, the indication unit comprises a display or is configured as a display.

Preferably, the indication unit comprises a mirror arrangement for mirroring the axis position or the orientation of the axis of astigmatism into the beam path of the observation unit or of the surgical microscope. In particular, the indication unit can be configured as a display including a mirror arrangement for mirroring into the beam path of the observation unit or of the surgical microscope. In particular, use can be made of relatively small displays, e.g. with dimensions of 2" to 3". However, further technologies may also be used for indication purposes.

Advantageously, a memory is provided for storing a value or a reference value, which represents the orientation of the axis of astigmatism of the eye at a first time. Consequently, this value characterizes the orientation of the axis of astigmatism that should be corrected by the operation and that is indicated in the image. In particular, the angular position of the axis of astigmatism is stored as a reference value.

Since steps which change the astigmatism are often carried out in the operation, the angle of the measured axis of astigmatism before carrying out such steps in the operation is stored as a reference value which represents the reference orientation of the axis of astigmatism. Consequently, steps in the operation that change the astigmatism cannot falsify the indication of the orientation of the axis of astigmatism to be corrected.

In particular, the memory moreover also serves to store a reference orientation of the observation unit or of the microscope or of the camera. Consequently, the orientation of the observation unit or of the microscope and/or of the camera that was valid at the time of the reference measurement of the orientation of the axis of astigmatism can be stored. Subsequently calculated microscope or camera orientations can relate to this stored orientation of the observation unit as a reference orientation.

By ascertaining the orientation of the axis of astigmatism by a first measurement or reference measurement and by subsequently evaluating the sensor signals for the purposes of ascertaining the change in orientation of the surgical microscope or the observation unit in relation to its orientation during the reference measurement, in particular, an increased robustness and a lower susceptibility to errors arises when calculating the current orientation of the axis of astigmatism in the image of the eye in relation to astigmatism-measuring methods or the application of image processing algorithms, the accuracy or success of which during the registration (or during the matching) of diagnostic image and current camera images may be negatively influenced by the image quality, the presence of occlusions and foreign objects such as, for example, surgical instruments, bleeding, etc.

The same advantage arises in relation to measuring systems since the results in that case are likewise based on the evaluation of camera images. Hence, all influences can be noticeable in negative fashion in the image of the eye or the visibility thereof.

A further advantage consists of the calculation duration of the proposed solution with sensors being significantly shorter on account of the much lower complexity, as a result of which there are shorter latencies when presenting the current axis of astigmatism. Moreover, the illumination of the eye can be drastically reduced after the reference measurement, leading to increased comfort for the patient.

Preferably, the sensor device ascertains the rotation of the observation unit about its observation direction and/or the position of the observation unit during operation. In particular, the rotation of the observation unit or the rotation and the position of the observation unit can be ascertained with the aid of the sensor device. Preferably, the sensor device in this case measures the angle of rotation of the surgical microscope or of the observation unit about the observation direction or about the optical axis of the surgical microscope.

The sensor device preferably measures angular speeds, as a result of which, in the case of continuous monitoring and corresponding positioning on the microscope or the observation unit, for example, the torsion thereof about the observation direction can be derived relative to the reference measurement.

Advantageously, the sensor device comprises one or more angular rate sensors, such as gyroscope sensors, for example, or one or more inertial measurement units, also referred to as IMUs, which, inter alia, also contain gyroscope sensors, for example. These sensors may also be combined with one another. In particular, this facilitates the calculation of the relative situation or alignment of the microscope or of the microscope camera in relation to a reference alignment.

Preferably, the sensor device comprises one or more acceleration sensors, compass sensors or direction sensors, which are also combinable among themselves. As a result, the calculation of the orientation and situation or position of the observation unit, in particular of the microscope or its constituent parts, can be simplified or improved. Errors such as a drift in the data, for example, are reduced or even eliminated.

Advantageously, the sensor device comprises sensors that measure a change in the joints of the observation unit or of the surgical microscope, with potentiometers or rotary encoders, in particular, being used to this end. This yields a particularly simple option for measuring the situation or direction or position, with these sensors or potentiometers or rotary encoders preferably being arranged at the joints of the surgical microscope and particularly preferably being integrated in the joints.

In particular, the sensor device comprises one or more sensors for ascertaining the alignment and/or position of the head of the patient.

In particular, either the alignment of the head or the alignment and the position of the head is/are measured. In particular, a twist or rotation of the head of the patient about the observation direction or about the optical axis of the observation unit or of the surgical microscope is measured in the process.

In the process, the patient or their head can be tracked or followed in respect of its situation. What this achieves is that a rotation of the head of the patient, and hence of their eye, about the optical axis of the microscope camera or of the observation direction is captured and taken into account in the calculation by the computing unit. That is to say, a rotation of the head of the patient does not bring about a falsification of the measurement result.

The observation direction or optical axis means the optical axis of the surgical microscope or, in general, of the observation unit, in particular, that corresponds to the observation direction defined, for example, by the optical axis of the entrance optical unit of the surgical microscope or of the observation unit.

Furthermore, provision can be made, in particular, of sensors for measuring the alignment and the position of the operating table, which carries the patient during the operation and on which the patient and their head, in particular, are secured. These sensors can be arranged either individually or in combination and can be configured as part of the entire sensor device. As a result, a falsification of the measurement results in the case of a change in the orientation of the patient table during the operation is avoided. This is particularly expedient if a relevant twist of the head about the viewing direction or the optical axis of the observation unit is physically impossible as a result of the manner of bearing the patient.

Preferably, the alignment or the position of the table of the patient, and consequently also its situation or orientation, is followed or tracked with the aid of the sensors.

In particular, a following or tracking device is provided, which tracks the alignment and position of the observation unit, in particular of the surgical microscope, and which tracks the situation, or alignment and position, of the head of the patient.

In this case, the orientation of the current axis of astigmatism to be indicated is calculated from the reference orientation of the axis of astigmatism, the orientation of the microscope or of the camera in relation to its orientation at the reference time and from the orientation of the head or the patient table, should the head be secured to the table, likewise in relation to the reference time. The reference position of the head or of the patient table are measured during the reference measurement of the axis of astigmatism, in a manner analogous to ascertaining the reference position or reference orientation of the microscope.

The computing unit is preferably configured in such a way that it determines the direction or orientation of the axis of astigmatism of the eye as an angular sum of the reference orientation or reference angle position of the axis of astigmatism and the angle position of the surgical microscope or the camera, calculated by means of the sensor unit, in relation to the optical axis relative to the angle position during the reference measurement. That is to say, the angular sum is formed from the angle of the axis of astigmatism at the first measurement time (=reference orientation) and the angle of a subsequently carried out rotation of the microscope or microscope camera about the observation direction, which is ascertained from the signals of the sensor device.

The method according to the invention for indicating the axis of astigmatism of the eye comprises the steps of: providing an observation unit for observing the eye; providing the orientation of the axis of astigmatism of the eye for presentation on an indication unit during the observation of the eye; capturing and storing sensor data, which characterize a change in the alignment of the observation unit in relation to the eye; and calculating and updating, with the aid of the sensor data, the orientation of the axis of astigmatism to be presented on the indication unit.

Preferably, the alignment of the observation unit in relation to the eye is ascertained at a first time T1 and at a second time T2, and the orientation of the axis of astigmatism A of the eye is ascertained from the sensor data and indicated at the second time T2.

In particular, the orientation of the axis of astigmatism at the first time T1 is used to ascertain the orientation of the axis of astigmatism, to be indicated, at the second time T2.

Advantageously, the alignment of the observation unit is tracked. In particular, the position and the alignment of the surgical microscope is tracked or followed.

Particularly preferably, the angle of rotation of the observation unit is captured about its observation direction or about its optical axis. In particular, the angle of rotation of the surgical microscope is ascertained about its observation direction or about its optical axis in order to determine the alignment of the surgical microscope or of the microscope camera.

Advantageously, the alignment and/or position of the head of the patient and/or of a patient table, on which the patient is secured, is measured in order to capture a twist of the head about the observation direction or the optical axis of the observation unit and use this in the calculation of the current orientation of the axis of astigmatism. The orientation of the head of the patient and/or of the table of the patient can also be tracked or followed in the process.

In particular, the current orientation, or currently calculated orientation, of the axis of astigmatism is displayed on a display, advantageously in a current image of the eye, and/or it is mirrored into the beam path of a surgical microscope. As a result, it can be updated in the case of a change in the alignment of the surgical microscope.

According to one aspect of the invention, a method for indicating the axis of astigmatism of the eye is exhibited, said method comprising the following steps:

capturing images of the eye using a surgical microscope and/or a camera; capturing a first measurement value that denotes the orientation of the axis of astigmatism in the image of the eye at a first time T1; capturing and storing the alignment of the surgical microscope at the first time; capturing the alignment of the surgical microscope at a second time T2; and indicating a corrected orientation of the axis of astigmatism A of the eye in the image of the eye at the second time T2, wherein the corrected orientation is ascertained from the first measurement value and from the alignment of the surgical microscope at the second time T2 or from the change in alignment of the surgical microscope in relation to the alignment at the time T1.

Preferably, the first measurement value is captured when the patient is in the operation position.

Advantageously, the first measurement value is captured before steps of the operation that change the axis of astigmatism are carried out.

Advantages and details that are described in conjunction with the apparatus and that will still be explained in more detail below also apply to the method according to the invention, and vice versa.

BRIEF DESCRIPTION OF THE DRAWINGS

The invention will be described in exemplary fashion below on the basis of the drawings. In the drawings.

DETAILED DESCRIPTION

Figure 1:
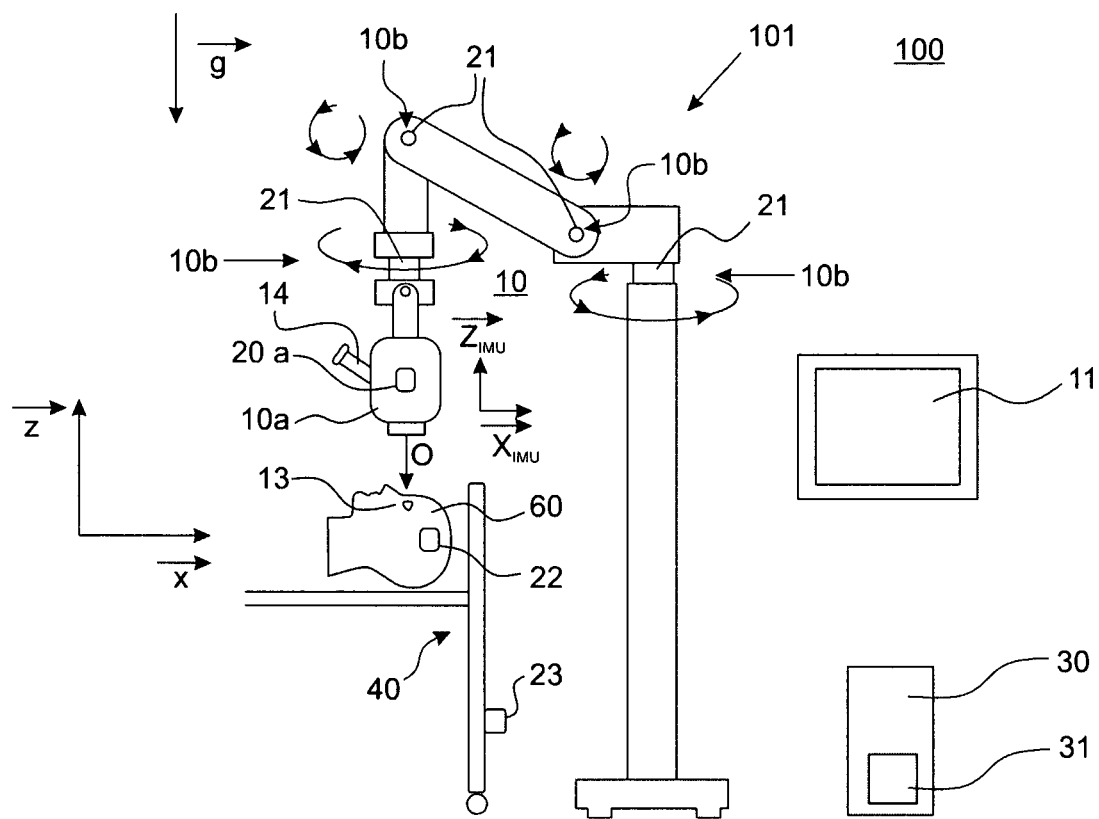
FIG. 1 shows an apparatus according to the invention in a schematic illustration.

FIG. 1 shows an apparatus 100, which serves to indicate the eye with its axis of astigmatism during eye surgery, as a preferred embodiment of the invention. Here, a microscope or surgical microscope 10 serves as an observation unit for observing the eye 13 of a patient. A camera is configured as an integrated component of the microscope head 10a and records images 12 of the eye 13 (see FIG. 3A). An indication unit 11 serves to indicate the orientation R of the axis of astigmatism A of the eye 13 in the presented or recorded images 12 of the eye, which is captured by the surgical microscope 10.

A sensor 20a facilitates the determination of the alignment or the situation of the surgical microscope 10. The sensor 20a is configured as an inertial measurement unit or IMU and continuously measures accelerations and angular speeds in respectively three degrees of freedom. However, it can also be configured as a separate rotational rate sensor or gyroscope sensor.

Figure 3A:
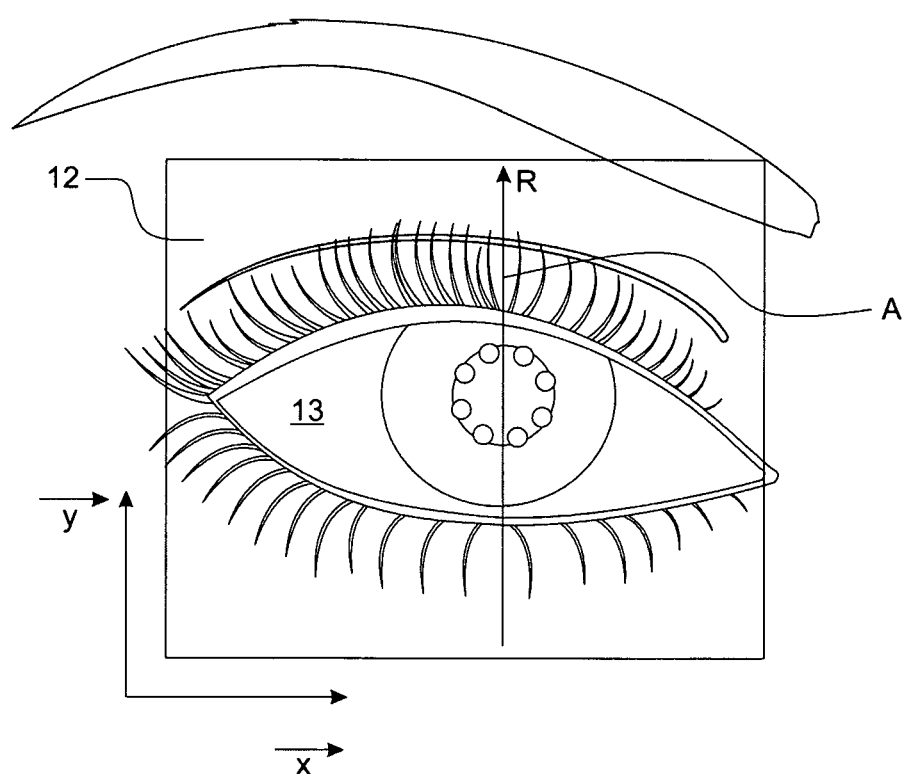
FIG. 3A shows a field of view of a microscope, which schematically shows the eye and the axis of astigmatism.
Figure 3B:
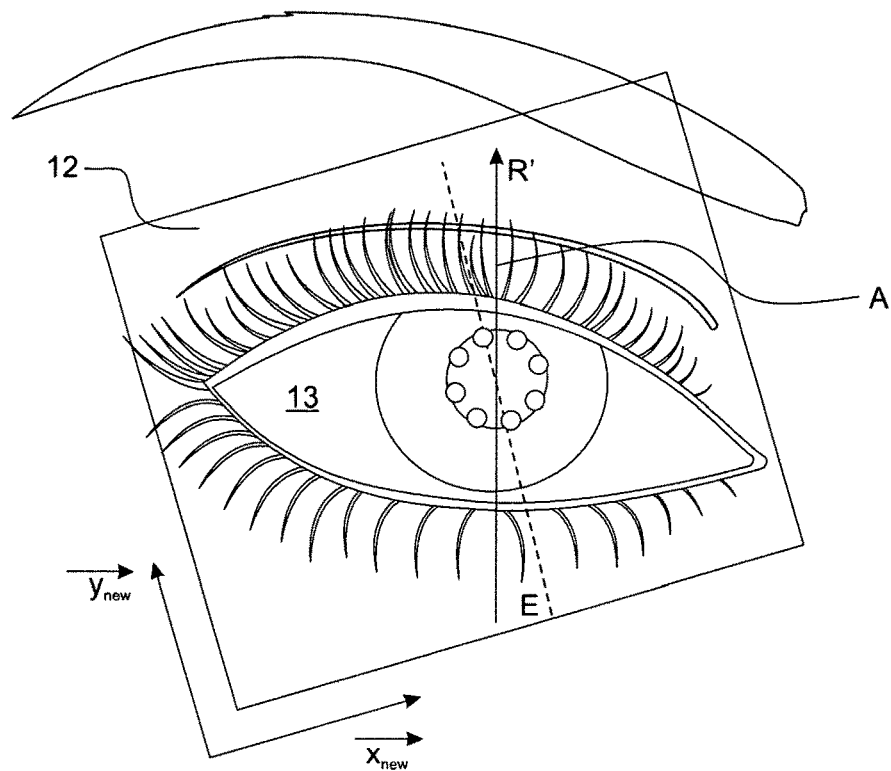
FIG. 3B shows the field of view according to FIG. 3A, albeit after a rotation of the surgical microscope about the gravitational vector.
Figure 3C:
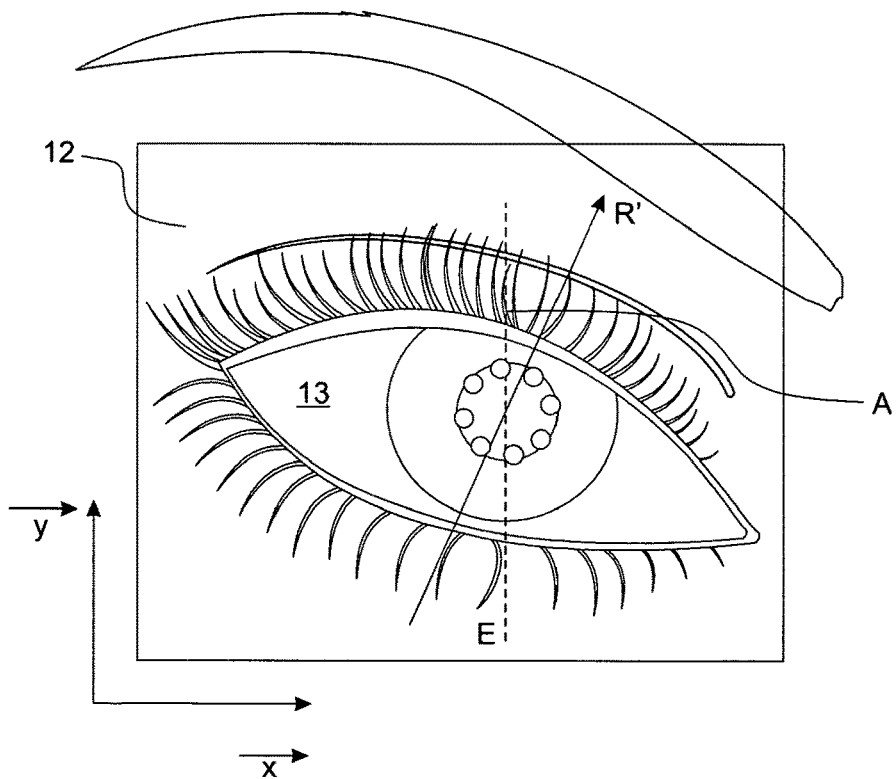
FIG. 3C shows the field of view according to FIG. 3A, albeit after a rotation of the patient head or the operating table about the gravitational vector.

Furthermore, a computing unit 30 is provided, which calculates the current orientation R' of the axis of astigmatism A in the respective current image 12 of the eye 13 (see FIGS. 3A to 3C). The calculation is implemented using the orientation R of the axis of astigmatism A of the eye 13 at a first time T1 and the respective alignment of the surgical microscope 10, derivable from the sensor data, at the first time T1 and at a second time T2, which is the current time. That is to say, the orientation R' of the axis of astigmatism is determined in the current image of the eye from the originally correctly determined orientation of the axis of astigmatism in the image 12 of the eye 13 and the subsequent change in the alignment of the surgical microscope 10.

The computing unit 30 may consist of a plurality of components. By way of example, this relates to one or more microcontrollers in combination with a PC. Here, the microcontrollers read the sensors and guide the data, either directly or in processed form, to the PC, which carries out the final calculations and forwards the results to the indication unit.

The computing unit 30 is coupled to the indication unit 11 in order to make the current orientation R' of the axis of astigmatism available to the indication unit 11.

The surgical microscope 10 comprises a holder 101 in the form of a carrying structure with a plurality of elements that are movable relative to one another and connected to one another in movable fashion by way of joints 10b. The central part of the surgical microscope 10 is formed by a microscope head 10a with an integrated camera, which is fastened in movable fashion to the holder 101.

Situated in the surgical microscope 10 there is an eyepiece 14, through which the physician observes the image of the eye 13 of the patient, magnified by the microscope, during the operation.

With its camera, the movable surgical microscope 10 is aligned on the eye 13 of the patient before and during the operation. This direction forms the observation direction O and corresponds to the optical axis of the light entrance optical unit of the surgical microscope 10 and of the camera integrated into the microscope head 10a.

Changes in the situation and/or alignment of the camera are measured using the sensor 20*a* fastened to the microscope head 10*a*. In the process, a rotation of the surgical microscope 10 about the observation direction O is captured. Provided the surgical microscope 10 is aligned on the eye 13 of the lying patient vertically from above, the observation direction O corresponds to the direction of the gravitational vector g, which extends counter to the Z-direction in FIG. 1.

The sensor 20*a* configured as an inertial measurement unit or as a rotational rate or gyroscope sensor measures the rotation or angular speed or rotational rate of the camera and of the microscope head 10*a* about the observation direction O, i.e., about the Z-direction in this case. By way of example, the relative angle position of the camera about the observation direction can be established therefrom with the aid of the computing unit 30.

In addition to the sensor 20*a* shown here, sensors 21 that measure the positioning of the joints 10*b* of the surgical microscope 10 are arranged in the preferred exemplary embodiment. The sensors 21 are configured as potentiometers or rotary encoders, which are arranged in the joints 10*b* of the surgical microscope 10 or the holder 101 thereof. As a result, rotational movements relative to one another of the partial elements of the holder 101 are captured, from which it is possible to determine the situation and alignment of the surgical microscope 10 or its camera 10*a*.

The sensors 21 for measuring the positioning of the joints 10*b* may be arranged in addition or as an alternative to the one or more rotational rate or gyroscope sensors 20*a*.

The preferred embodiment of the invention illustrated here additionally comprises one or more sensors 22, which are fastened to the head 60 of the patient and measure or capture a rotation of the head 60 of the patient about the observation direction O. The sensors 22 are preferably rotational rate or gyroscope sensors, or they are configured as inertial measurement units or IMUs. As a result, a rotation of the head 60 of the patient during the operation can be taken into account when determining the orientation of the axis of astigmatism A of the eye in the displayed image 12 of the eye.

An operating table 40 serves to bear the patient during the operation. Here, the patient is usually fastened to the operating table 40 in such a way that the head 60 of the patient cannot move or is secured to the operating table 40.

The apparatus shown here as a preferred example furthermore comprises a sensor 23 that measures the alignment and/or the position of the operating table 40. Rotations of the table about the gravitational direction Z or about the observation direction O are of particular importance in this case. That is to say, the operating table 40 can be tracked in terms of its position and situation or orientation with the aid of the one or more sensors 23 should it not be possible to preclude a change in orientation of the operating table 40 during the operation. This is particularly expedient if a relevant twist of the head 60 about the optical axis of the observing microscope camera is made physically impossible by the way the patient is borne, i.e., if the head 60 of the patient is fastened to the operating table 40 in such a way that it cannot move relative to the latter.

Consequently, the head 60 of the patient can likewise be followed or tracked in space, in a manner analogous to the surgical microscope 10 or the camera integrated in the microscope head 10*a*. If a twist of the head of the patient relative to the table is made impossible by the method of bearing, it is sufficient for either the head or the table to be equipped with a sensor.

The sensors 20*a*, 21, 22, 23 can be arranged individually or combined with one another in order to capture the relative rotation between the operating camera and the eye 13 about the observation direction θ. They form, either individually or in combination, a sensor device 20. The latter is coupled to the computing unit 30 in such a way that the signals of the sensors 20*a*, 21, 22, 23 are transferred to the computing unit 30. This is implemented by means of an electrical connection, which may also be wireless.

The computing unit 30 calculates the current orientation R' of the axis of astigmatism A in the image 12 of the eye 13 during the course of the eye surgery. The current orientation R' of the axis of astigmatism A corresponds to the actual orientation R of the axis of astigmatism for as long as there is no change in the alignment or situation of the surgical microscope 10 in relation to the eye 13 of the patient. However, this assumes that the actual orientation of the axis of astigmatism, which was ascertained in diagnostic fashion prior to the operation, has not been modified by certain steps in the operation. The calculation will still be explained in more detail below with reference to FIGS. 3A, 3B, 3C.

The computing unit 30 contains a memory 31 which, inter alia, stores the orientation R of the axis of astigmatism A of the eye as a reference value for the subsequent calculations. Likewise, the measurement values ascertained by the sensor device 20, which serve to calculate the current orientation R', are saved in the memory.

The indication unit 11 is coupled to the computing unit 30 in order to indicate the calculated orientation R' of the axis of astigmatism A in the image 12 of the eye 13. By way of example, the indication unit 11 is a display that reproduces the image that is recorded by the camera integrated in the microscope head 10*a*. In addition to the image recorded thus, the axis of astigmatism A is illustrated or superposed on the image 12 of the eye 13 with the current orientation R' calculated by the computing unit 30.

However, it is also possible for the indication unit 11 to be able to be observed through the eyepiece of the surgical microscope 10 or to be integrated into the surgical microscope 10.

Figure 2:
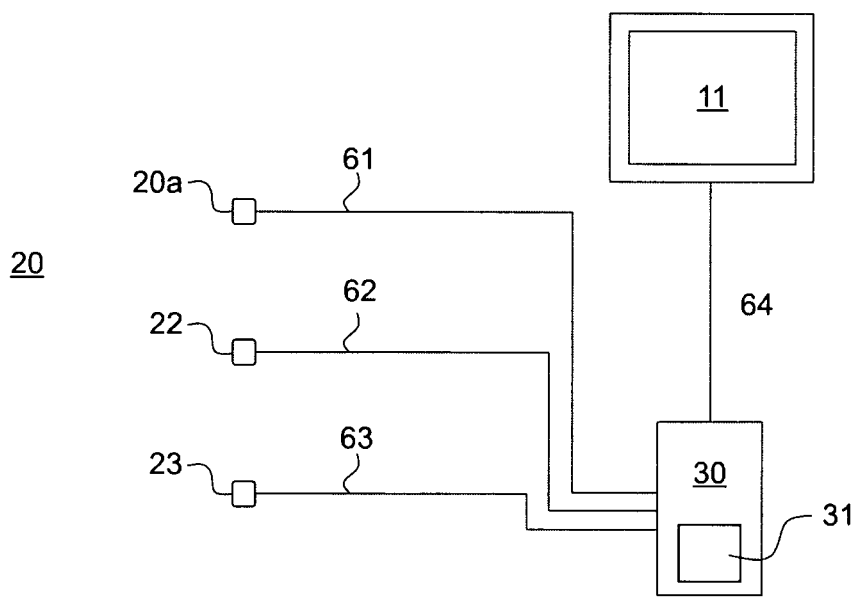
FIG. 2 shows an exemplary sensor arrangement with a computing unit and indication unit in a schematic illustration.

FIG. 2 shows the computing unit 30, the indication unit 11 and the sensors 20*a*, 22 and 23, as described above with reference to FIG. 1, in detail. The sensors 20*a*, 22, 23 form the sensor device 20, or are part thereof, and are configured as rotational rate or gyroscope sensors or as IMUs. The at least one sensor 20*a* is arranged on the microscope head 10*a* in order to ascertain the alignment or situation thereof with the aid of the computing unit while the one or more sensors 22 or 23 are fastened to the head 30 of the patient or to the operating table 40 in order to facilitate the ascertainment of the alignment or situation of the head 60 or of the operating table 40.

The computing unit 30 continuously reads the angular speeds measured by the gyroscopes or the IMUs and calculates the alignment in relation to a reference alignment therefrom.

The sensors of the sensor device 20 are connected to the computing unit 30 by way of electrical connections 61, 62, 63. The electrical connections can also have a wireless configuration. They serve to transfer the sensor signals to the computing unit 30.

The computing unit 30 is connected to the indication unit 11 by way of a further electrical connection 64, which has a wireless configuration, for example. The computing unit 30 produces signals for actuating the indication unit 11 in order to indicate there the respective current orientation R' of the axis of astigmatism A in the image 12 of the eye 13, said current orientation being calculated from the values measured by the sensors.

FIG. 3A shows the field of view of the microscope camera, in which the image 12 of the eye 13 of the patient is situated. The field of view is presented on the indication unit 11 (see FIG. 1). The axis of astigmatism A of the eye 13 is likewise presented in the image 12, said axis of astigmatism being aligned in approximately the Y-direction in the illustrated example.

FIG. 3B shows the field of view of the microscope camera, with, however, the indicated image 12 having been twisted in this case about the Z-direction, which extends perpendicular to the plane of the image. In this case, this torsion of the image about the Z-direction is caused by the surgical microscope 10 being twisted about the observation direction O in the counterclockwise direction (see FIG. 1), for example. As a result of the torsion of the image 12, the eye 13 is illustrated twisted in the clockwise direction in the image 12.

Without the calculation and correction, according to the invention, of the indicated orientation of the axis of astigmatism A, the latter would not co-rotate with the image and would consequently be indicated incorrectly. This incorrectly indicated orientation is represented by the dashed line E in FIG. 3D. The error that would arise therefrom corresponds to the angle of rotation $\alpha$, i.e., the angle of the rotation of the surgical microscope 10 or of the image 12.

$$\alpha = \text{angle}(\vec{y}, \vec{y}_{new}) \text{ or } \alpha = \text{angle}(\vec{x}, \vec{x}_{new})$$

Now, the computing unit 30 calculates the new or corrected orientation R' or angle position of the axis of astigmatism A in the image 12 from the signals supplied by the sensor device 20 such that said axis of astigmatism is represented correctly in relation to the eye 13, i.e., relative to the eye 13. The correction angle corresponds to the angle $\alpha$, i.e., the angle through which the image 12 has rotated in relation to its initial position.

FIG. 3C shows, in exemplary fashion, the case where the head 60 of the patient has rotated about the observation direction O. This may have been caused by the patient themselves and/or by a rotation of the operating table 40 about the observation direction O. In this example, the assumption is made that there has been no change in the alignment of the surgical microscope 10.

As a consequence of the rotation of the head 60, the alignment of the eye 13 in the image 12, or of the axis of astigmatism, no longer corresponds to the original alignment, i.e., the eye 13 is presented in twisted fashion in the image 12. Without the calculation according to the invention of the orientation of the axis of astigmatism A, the latter would be illustrated erroneously once again, as shown by the dashed line E. That is to say, it would continue to be indicated as extending approximately parallel to the direction of the y-axis of the image in this example, as its situation in the image 12 was ascertained originally or prior to the twist of the head 60 (see FIG. 3A).

Now, this error is corrected with the aid of the sensor device 20 and the computing unit 30. The actual, current alignment or orientation of the axis of astigmatism A of the eye is calculated by virtue of its angle position being corrected by the angle $\beta$.

This angle $\beta$ corresponds to the angle of rotation of the head 60 about the observation direction O.

$$\beta = \text{angle}_{rot}(\text{head})$$

If the head is borne in such a way that a twist relative to the patient table is not possible due to securing, a head sensor can be dispensed with. Instead, use can be made of a sensor attached to the table for the purposes of determining a rotation of the head and hence of the eye. In such a case, $\beta$ corresponds to the angle of rotation of the patient table.

$$\beta = \text{angle}_{rot}(\text{table})$$

An additional head sensor would be redundant since the latter would measure the same rotation or the same rotational rate or angular speed about the observation direction as the sensor on the table, i.e., the same angle $\beta$ arises:

$$\beta = \text{angle}_{rot}(\text{table}) = \text{angle}_{rot}(\text{head})$$

As a consequence of this calculation, the axis of astigmatism A is indicated in the direction R' in the image 12. On account of the implemented calculation or the actual orientation, the orientation R' corresponds to the axis of astigmatism A of the eye, which was diagnosed previously.

The individual steps of the method are explained below:

In order to indicate the axis of astigmatism of the eye during an eye operation, an image 12 of the eye 13 is initially captured using the surgical microscope 10. This is implemented at a time T1, at which no rotation of the surgical microscope 10 has yet taken place relative to the eye 13 of the patient. A first measurement value, which denotes the orientation R of the axis of astigmatism A in the image 12, is captured in this state. Consequently, the orientation R of the axis of astigmatism A in the image 12 of the eye 13 at the time T1 corresponds to the actual orientation (see FIG. 3A). In the example illustrated in FIG. 3A, this is approximately 90 degrees in relation to the x-axis of the image.

Now, the angle position OP1 of the microscope head 10*a* about the observation direction at this first time is initialized at 0 degrees, for example, and stored as a reference orientation, i.e., OP1: =0 degrees.

Now, the angle position or rotation OP2 of the microscope head 10*a*, and hence of the integrated camera, about the observation direction is ascertained anew during the operation, i.e., at a subsequent, second time T2. At this time, the microscope head 10*a*, and hence the integrated camera, was rotated through, for example, 30 degrees counterclockwise about the z-axis. The new alignment of the camera in relation to the alignment at the time T1 corresponds to the angle OP2−OP1, which is plus 30 degrees in this case, i.e., OP2−OP1=+30 degrees.

The sign is positive since rotation of the surgical microscope 10 was implemented counterclockwise about the z-axis. The angle of the rotation of the surgical microscope 10 is:

$$\alpha = \Delta OP = OP2 - OP1,$$

i.e., in this example: $\Delta OP = +30$ degrees−0 degrees, i.e., $$\alpha = +30 \text{ degrees.}$$

As a result, the orientation of the eye 13 in the image is rotated through 30 degrees clockwise (see FIG. 3B). That is to say, the implemented rotation of the eye in the image 12 at the time T2 is:

$$\Delta A = -\Delta OP, \text{ i.e., } \Delta A = -30 \text{ degrees in this case.}$$

Subsequently, the corrected orientation R' of the axis of astigmatism A in the image 12 is calculated. To this end, the first measurement value is initially considered, the latter denoting the orientation R of the axis of astigmatism A in the image 12 at the first time T1. That is to say, R=90 degrees in this example. The angle AA is added to the angle R which denotes the original orientation R of the axis of astigmatism at the time T1:

$$R'=R+\Delta A, \text{ or}$$

$$R'=R-\Delta OP=R-(OP2-OP1)=R-\alpha=90 \text{ degrees}-30 \text{ degrees}=60 \text{ degrees}$$

The orientation R' of the axis of astigmatism A of the eye 13 at the time T2, calculated thus, is indicated in the image 12 of the eye by means of the indication device.

The angle of the implemented relative rotation between the operating microscope 10 or the camera in 10a in relation to the eye 13 may however emerge, as illustrated at the top in FIG. 3C, not only from a rotation of the surgical microscope 10 with the camera but also from a rotation of the head 60 of the patient.

In this case, R' emerges as follows:

$$R'=R+\beta,$$

where β denotes the angle of the implemented rotation of the head 60 about the z-direction or about the direction of the gravitational vector g.

The corrected angle for the representation of the axis of astigmatism R' in the image 12 of the eye 13, taking account of all rotations, emerges from:

$$R'=R-\alpha+\beta.$$

Capturing the angle position and calculating R' can also be implemented repeatedly or continuously, i.e., the position or alignment of the surgical microscope 10 is followed or tracked throughout the course of the operation. That is to say, the alignment or situation and position of the surgical microscope 10, of the head 60 of the patient and of the operating table 40 are advantageously measured multiple times during the operation and tracked in this manner such that the orientation R' of the axis of astigmatism A is correctly presented in the image 12 of the eye at all times during the operation, independently of what torsions about the observation direction O have taken place in the meantime.

Provided the situation or alignment of the axis of astigmatism of the eye changes due to appropriate surgical interventions, as may be the case for incisions at the edge of the iris, for example, the previously determined, preoperative situation of the axis of astigmatism A is nevertheless presented on the indication unit 11 since there is no new measurement of the axis of astigmatism on the eye during the operation. Instead, the starting point always is the original axis of astigmatism A with the original orientation R in the illustrated image and the relative rotation between surgical microscope 10 or the camera in 10a and the eye 13 about the observation direction Z, which subsequently takes place during the operation.

The apparatus according to the invention and the method according to the invention offer the advantage that a diagnostic image is not necessary.

Despite a possible change in the orientation of the axis of astigmatism by steps in the operation, the orientation of the preoperative axis or the intended orientation of the IOL to be implanted can be indicated at all times. Ascertaining the orientation of the axis of astigmatism A by a reference measurement and a subsequent evaluation of sensor signals is far less complex and susceptible to errors than a continuous, camera-based direct measurement or the application of image processing algorithms, the accuracy of which can be influenced negatively during the registration of diagnostic image with current camera images by the image quality, the presence of foreign objects, such as, for example, surgical instruments, occlusions or bleeding, etc.

The invention claimed is:

1. An apparatus for indicating an axis of astigmatism of an eye, the apparatus comprising:
    an observation unit for observing the eye;
    an indication unit for indicating orientation of the axis of astigmatism of the eye;
    a sensor device comprising at least one angular rate sensor configured to detect a rotation of the observation unit about its observation direction and produce sensor data that characterize a change in alignment of the observation unit in relation to the eye, wherein the sensor data is produced from the rotation of the observation unit about its observed direction; and
    a computing unit, which is configured to update the orientation of the axis of astigmatism and provide the orientation of the axis of astigmatism to the indication unit as a current orientation of the axis of astigmatism for indication by the indication unit, wherein the orientation of the axis of astigmatism is updated with aid of the sensor data and from the rotation of the observation unit about its observation direction.

2. The apparatus as claimed in claim 1, wherein the observation unit comprises or is configured as a surgical microscope.

3. The apparatus as claimed in claim 1, wherein the observation unit comprises or is configured as a device for recording images of the eye.

4. The apparatus as claimed in claim 1, wherein the indication unit is configured as a display.

5. The apparatus as claimed in claim 1, wherein the indication unit comprises a mirror arrangement for mirroring into a beam path of the observation unit.

6. The apparatus as claimed in claim 1, comprising a memory for storing a reference value, which represents the orientation of the axis of astigmatism of the eye at a first time, and/or for storing a reference orientation of the observation unit.

7. The apparatus as claimed in claim 1, wherein the sensor device is configured to ascertain a position of the observation unit.

8. The apparatus according to claim 1, wherein the sensor device comprises one or more inertial measurement units.

9. The apparatus according to claim 1, wherein the sensor device comprises one or more sensors selected from the group consisting of acceleration sensors, direction sensors, and compass sensors.

10. The apparatus as claimed in claim 1, wherein the sensor device comprises sensors for measuring a positioning of joints of the observation device.

11. The apparatus as claimed in claim 1, wherein the sensor device comprises one or more sensors for ascertaining an alignment and/or a position of a head of the patient.

12. The apparatus as claimed in claim 1, wherein the sensor device comprises one or more sensors for ascertaining an alignment and/or a position of an operating table.

13. The apparatus as claimed in claim 1, comprising a device for tracking a position and/or an alignment of the observation unit and/or an alignment and/or a position of a head of the patient.

14. A method for indicating an axis of astigmatism of the eye, the method comprising:
    providing an observation unit for observing an eye;
    providing orientation of the axis of astigmatism of the eye for presentation on an indication unit during observation of the eye;

capturing and storing sensor data, which characterize a change in alignment of the observation unit in relation to the eye; and calculating and updating, with aid of the sensor data, an orientation of an axis of astigmatism to be presented on the indication unit;

wherein the alignment of the observation unit in relation to the eye is ascertained at a first time and at a second time and the orientation of the axis of astigmatism of the eye is ascertained from the sensor data and indicated at the second time.

15. The method as claimed in claim 14, wherein the orientation of the axis of astigmatism at the first time is used to ascertain the orientation of the axis of astigmatism, to be indicated, at the second time.

16. The method as claimed in claim 14, wherein the alignment of the observation unit is tracked.

17. The method as claimed in claim 14, wherein an angle of rotation of the observation unit is captured about its observation direction or about its optical axis.

18. The method as claimed claim 14, wherein the alignment and/or position of a head of a patient and/or of a patient table is measured in order to capture a twist of the head about an observation direction or an optical axis of the observation unit and use this in calculation of current orientation of the axis of astigmatism.

19. The method as claimed in claim 14, wherein a current orientation of the axis of astigmatism is displayed on a display, in particular in a current image of the eye, and/or mirrored into a beam path of a surgical microscope.

20. A method for indicating an axis of astigmatism of the eye, the method comprising:

providing an observation unit for observing an eye;

providing orientation of the axis of astigmatism of the eye for presentation on an indication unit during observation of the eye;

capturing and storing sensor data, which characterize a change in alignment of the observation unit in relation to the eye; and calculating and updating, with aid of the sensor data, an orientation of an axis of astigmatism to be presented on the indication unit;

wherein the alignment and/or position of a head of a patient and/or of a patient table is measured in order to capture a twist of the head about an observation direction or an optical axis of the observation unit and use this in calculation of current orientation of the axis of astigmatism.

* * * * *